(12) United States Patent
Ettlinger et al.

(10) Patent No.: US 6,780,383 B1
(45) Date of Patent: Aug. 24, 2004

(54) SYSTEM FOR STERILIZATION OF SPACES AND SURFACES

(76) Inventors: Eugene Ettlinger, 2575 Palisades Ave., Riverdale, NY (US) 10463; Shirley Basso, 319 Ferndale Blvd., Islip, NY (US) 11751; Steven Brown, 130 Brook Ave., Deer Park, NY (US) 11729

(*) Notice: Subject to any disclaimer, the term of this patent is extended or adjusted under 35 U.S.C. 154(b) by 0 days.

(21) Appl. No.: 10/375,983

(22) Filed: Feb. 28, 2003

(51) Int. Cl.$^7$ .................................................. A61L 2/00
(52) U.S. Cl. ........................ 422/292; 43/132.1; 422/300
(58) Field of Search .............................. 422/1, 28, 292, 422/300; 43/132.1

(56) References Cited

U.S. PATENT DOCUMENTS

| | | | | |
|---|---|---|---|---|
| 4,434,890 A | * | 3/1984 | Sleck et al. ................. | 206/443 |
| 4,763,791 A | * | 8/1988 | Halverson et al. .......... | 206/570 |
| 4,882,873 A | * | 11/1989 | Purnell ....................... | 43/132.1 |
| 5,053,321 A | * | 10/1991 | Kuhnert ....................... | 430/450 |
| 5,456,036 A | * | 10/1995 | Butz ............................... | 43/1 |

* cited by examiner

Primary Examiner—Krisanne Thornton
(74) Attorney, Agent, or Firm—Ilya Zborovsky

(57) ABSTRACT

A system of sterilization of spaces and surfaces which includes a container having a plurality of walls which jointly define an inner chamber, a cover connected with the container turnably between an open position in which the inner chamber of the container is open and a closed position in which the inner chamber is closed; a plurality of compartments formed in the inner chamber and including a sprayer compartment; a mask compartment, a glove compartment, at least one encapsulant compartment, and a fungicide compartment which are separate from one another and do not communicate with one another; a uniform compartment provided in the cover; means for locking the cover with the container and unlocking the cover from the same; and elements for sterilization including a sprayer removably arranged in the sprayer compartment, a mask removably arranged in the mask compartment an encapsulant removably arranged in the at least one encapsulant compartment, a fungicide removably arranged in the fungicide compartment, at least one glove arranged in the glove compartment, and a uniform arranged in the uniform compartment.

6 Claims, 3 Drawing Sheets

SYSTEM FOR STERILIZATION OF SPACES AND SURFACES

BACKGROUND OF THE INVENTION

The present invention relates to a system for sterilization of spaces and surfaces.

It is known that some spaces and surfaces are contaminated with various types of bacteria, mold, etc. It is therefore necessary to decontaminate such spaces and surfaces with the use of corresponding decontamination means. When a professional or a general user has to decontaminate a space or a surface, he must uses various substances, as well as corresponding protective gear, which he obtains individually and use during the process of decontamination. It is believed that it is advisable to provide a system which would satisfy all needs for decontamination of corresponding spaces and surfaces.

SUMMARY OF THE INVENTION

Accordingly, it is an object of the present invention to provide a system for sterilization or decontamination of spaces and surfaces which efficiently performs its intended functions.

In keeping with these objects and with others which will become apparent hereinafter, one feature of the present invention resides, briefly stated, in a system of sterilization of spaces and surfaces, which includes a container having a plurality of walls which jointly define an inner chamber, a cover connected with said container turnably between an open position in which said inner chamber of said container is open and a closed position in which said inner chamber is closed; a plurality of compartments formed in said inner chamber and including a sprayer compartment; a mask compartment, a glove compartment, at least one encapsulant compartment, and a fungicide compartment which are separate from one another and do not communicate with one another; a uniform compartment provided in said cover; means for locking said cover with said container and unlocking said cover from the same; and elements for sterilization including a sprayer removably arranged in said sprayer compartment, a mask removably arranged in said mask compartment, an encapsulant removably arranged in said at least one encapsulant compartment, a fungicide removably arranged in said fungicide compartment, at least one glove arranged in said glove compartment, and a uniform arranged in said uniform compartment.

When the system is designed in accordance with the present invention, it includes a mobile container closeable by the cover which can be easily carried by a user, and all materials, equipment and gear necessary for providing sterilization of spaces and surfaces.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1A:
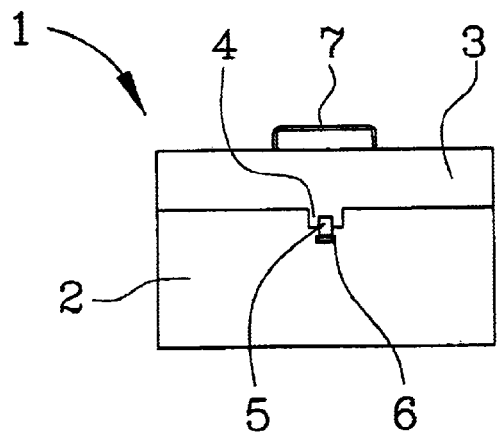
FIGS. 1a, 1b, 1c are three views showing a container with a cover of a system in accordance with the present invention.
Figure 1B:
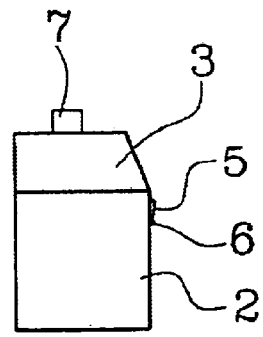
Figure 1C:
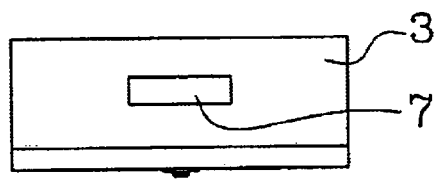
Figure 2:
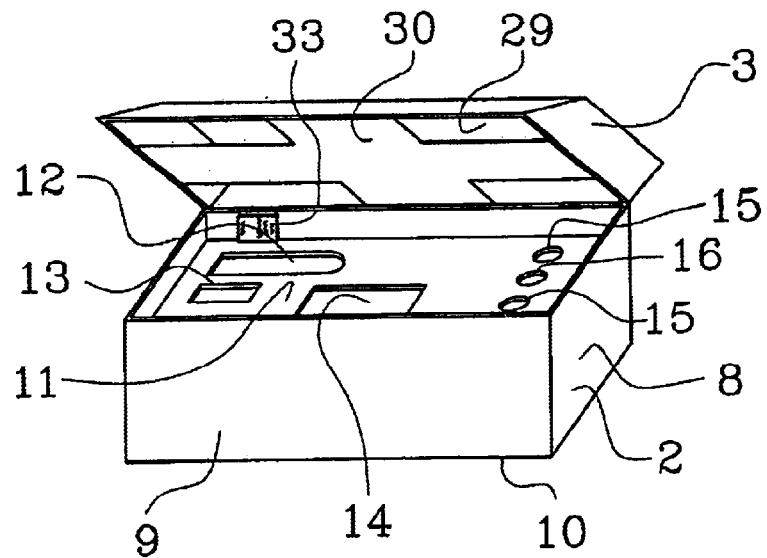
FIG. 2 is a perspective view of the inventive system with a cover turned so that the container is open.

A system in accordance with the present invention is identified as a whole with reference numeral 1. It has a container 2 and a cover 3. The cover 3 is turnable relative to the container 2 between an open position in which the container 2 is open as shown in FIG. 2 and a closed position in which the container 2 is closed as shown in FIGS. 1a–1c. The cover 3 can be turnable on hinges provided between the cover 3 and the container 2, for example a film hinge extending along the connecting line between the cover and the container. Locking means are further provided for locking the cover with the container in a position in which the system has to be transported. The locking means can include a projection 4 formed on the cover 3 and extending over a side surface of the container 2 and also provided with a tongue 5 and a buckle 6 provided on the side surface of the container 2, so that the tongue 5 can extend into the buckle to achieve locking action.

It is to be understood that other variants are also possible, for example it is possible to use a velcro connection between the projection 4 of the cover 3 at the side wall of the container 2. A handle 7 is provided on the cover 3 to facilitate opening of the cover and also to allow carrying of the container 2 with the closed cover 3 to corresponding locations.

The container 2 has a plurality of walls including two shortwalls 8 and two long walls 9 as well as a bottom 10 which together form an inner chamber of the container 2. The bottom 10 is substantially horizontal, and an intermediate partition which is also substantially horizontal is provided at a location which is upwardly spaced from the bottom 10. The intermediate partition 11 can be attached to the walls by known means, for example by glue, etc.

Figure 3:
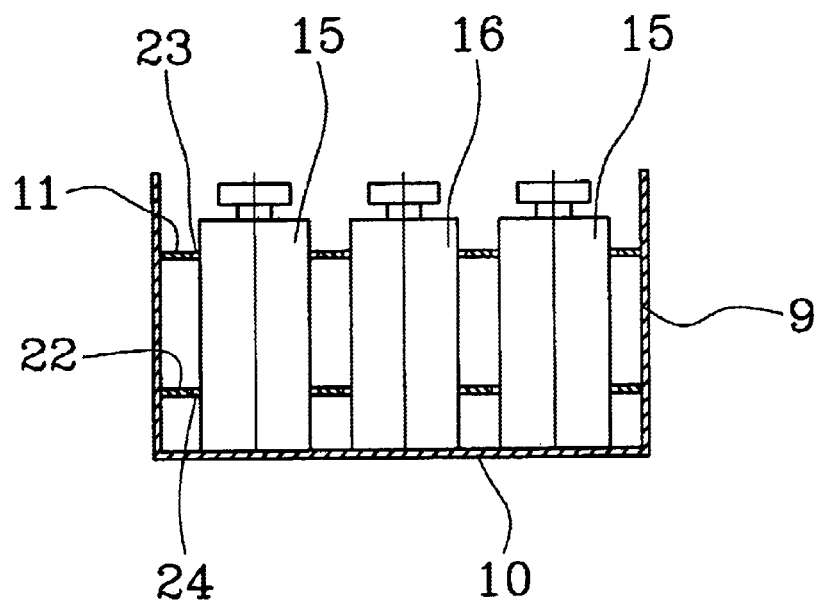
FIGS. 3–8 are views showing sections taken along the lines III—III, IV—IV, V—V, VI—VI, VII—VII and VIII—VIII in FIG. 2.

The inner chamber of the container 2 has a plurality of compartments including a sprayer compartment 12, a mask compartment 13, a glove compartment 14, two encapsulant compartments 15 and a fungicide compartment 16. The system further has a plurality of elements which are necessary for sterilization of spaces and surfaces. A sprayer 17 is arranged in the sprayer compartment 12, a mask 18 is arranged in the mask compartment 13, boxes with gloves 19 are arranged in the glove compartment 14, encapsulant bottles 20 are arranged in the encapsulant compartments 15, and a fungicide bottle 21 is arranged in the fungicide compartment 16. As can be seen from FIG. 3 in the region of the encapsulant compartments 15 and the fungicide compartment 16 another substantially horizontal intermediate wall 22 is provided between the partition 11 and the bottom 10 of the container. Therefore the bottles of the encapsulant 20 and the bottle of the fungicide 21 are reliably supported in their vertical position when the bottles are inserted through the holes 23 and 24 formed in the partitions 11 and 22 and the bottom of the bottles is supported on the bottom 10 of the container 2.

Figures 6, 7:
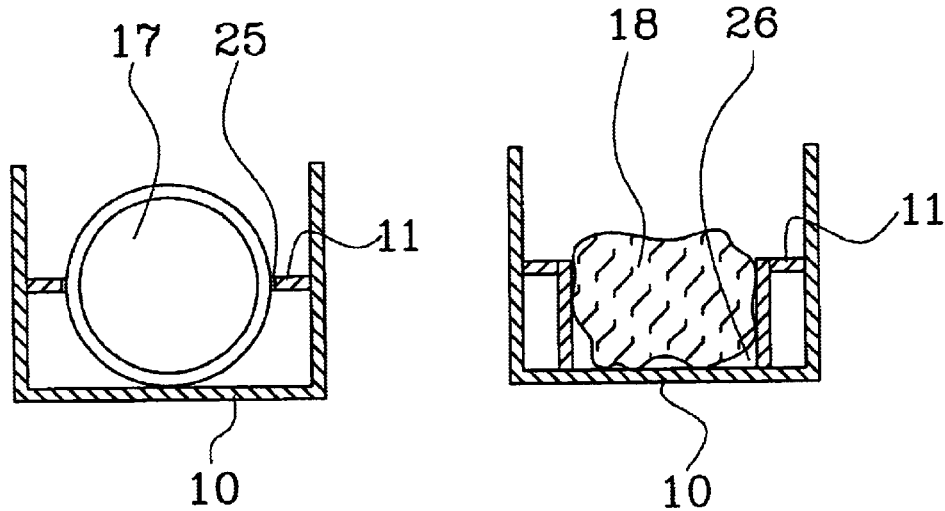
Figure 8:
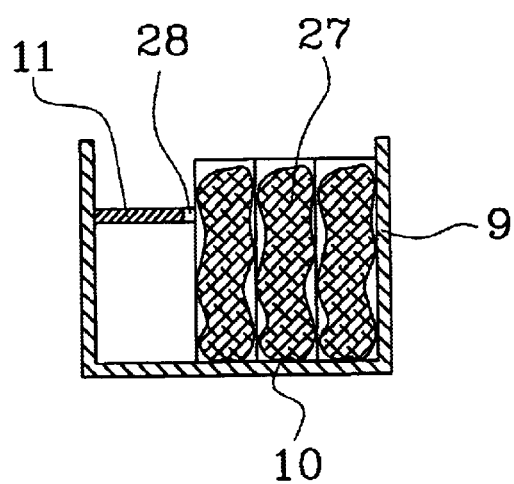

The sprayer 17 is inserted in the opening 25 in the intermediate partition 11 and rests on the bottom 10 of the container 2 as shown in FIG. 6. The mask 18 is folded and inserted in the opening 26 formed in the partition 11 so as to rest on the bottom 10 of the container 2.

The gloves 19 are located in the boxes 27 and the boxes, for example three boxes are arranged side by side in the opening 28 of the partition 11 so as to be supported on the bottom 10 of the container 2. The opening 14 is open at the front wall 9 so that the front box 27 also abuts against the vertical front wall 9 of the container 2. As can be seen from the drawings, the compartments 12, 13, 14, 15 and 16 are separated from one another by the material of the partition 11.

Figure 4:
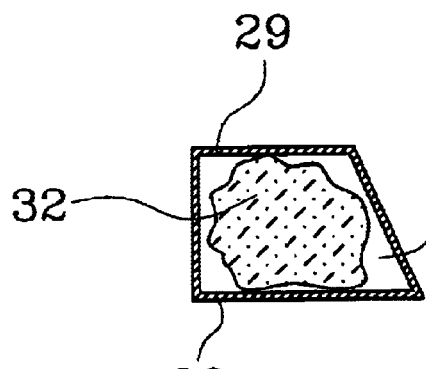
Figure 5:
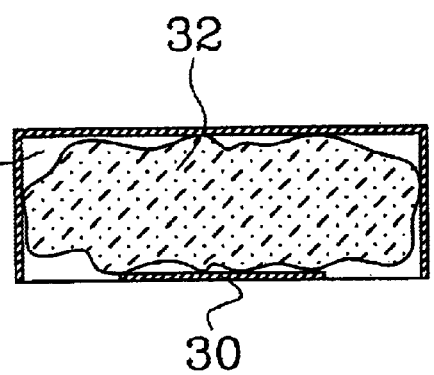

The cover 3 has an upper wall 29 and an intermediate wall 30 which is spaced downwardly from the upper wall 29 so as to form therebetween a uniform compartment as shown in FIGS. 4 and 5. A uniform 32 is folded and inserted in the compartment 31 of the cover 3 so as to be stored there.

Finally, an instruction booklet 33 is placed in the interior of the container near its rear wall.

When it is necessary to transport a system to a location of use, the container 2 is closed by the cover 3, and a user holds the system by grasping the handle 7 and transports it correspondingly. At the location of use, the user unlocks the locking means 4, 5, 6 and opens the cover 3. The user removes the uniform 32 and puts it on his body, then he removes a pair of gloves from one of the boxes 27 and puts the gloves on his hands, and finally he removes the mask 18 from the compartment 13 and places on his face. The user is therefore ready for performing corresponding sterilizing or remediating operation. The user when necessary removes a bottle with fungicide 21, removes the spray 17 from the compartment 12, and pours the fungicide composition into the sprayer 17. Then he activates the sprayer 17 and sprays the fungicide in a corresponding space or on a corresponding surface. When necessary, the user removes the bottle of encapsulant 20 from one of the compartments 15, puts the encapsulant composition into the sprayer 17, and sprays the encapsulant onto the walls of the space or other surfaces to provide encapsulation of the walls and surfaces thus preventing future contamination of the walls and surfaces.

It will be understood that each of the elements described above, or two or more together, may also find a useful application in other types of constructions differing from the types described above.

While the invention has been illustrated and described as embodied in system for sterilization of spaces and surfaces, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A system of sterilization of spaces and surfaces from bacteria, mold, etc., comprising a container having a plurality of walls which jointly define an inner chamber, a cover connected with said container turnably between an open position in which said inner chamber of said container is open and a closed position in which said inner chamber is closed; a plurality of compartments formed in said inner chamber of said container and including a sprayer compartment, a mask compartment, a glove compartment, at least one encapsulant compartment, and a fungicide compartment which are separate from one another, are horizontally spaced from one another and do not communicate with one another; single uniform compartment provided in said cover; means for locking said cover with said container and unlocking said cover from the same; and elements for sterilization including a sprayer removably arranged in said sprayer compartment of said container, a mask removably arranged in said mask compartment, of said container an encapsulant removably arranged in said at least one encapsulant compartment of said container, a fungicide removably arranged in said fungicide compartment of said container, at least one glove arranged in said glove compartment, and a uniform arranged in said single uniform compartment of said cover.

2. A system as defined in claim 1, wherein said container has a substantially horizontal bottom, and a substantially horizontal partition which is vertically upwardly spaced from said bottom so as to form a space between said bottom and said partition and provided with a plurality of throughgoing openings, said openings forming said compartments of said container and being separated from one another by material of said partition; and an additional partition which is located between said first mentioned partition and said bottom, said compartments for said encapsulants and said fungicides are formed as throughgoing holes in said first mentioned partition and said additional partition.

3. A system as defined in claim 2, wherein said partition and said openings are formed so that said elements are inserted in said throughgoing openings and rest on said bottom of said container.

4. A system as defined in claim 1, wherein said cover has a top wall and an intermediate wall which is vertically downwardly spaced from said top wall so as to form said uniform compartment therebetween, said cover being elongated, and said uniform compartment extending in a direction of elongation of said cover substantially over a whole length of the cover.

5. A system as defined in claim 1, wherein a container has a substantially horizontal bottom, and a substantially horizontal partition which is vertically upwardly spaced from said bottom so as to form a space between said bottom and said partition and provided with a plurality of throughgoing openings, said glove compartment being formed as one of said openings in said horizontal partition and being open toward one of said walls of said container, so that a box with at least one glove is arranged in said one opening so as to be supported on said bottom of said container and at the same time to be supported laterally on said wall of said container.

6. A system for sterilization of spaces and surfaces from bacteria, mold, etc., comprising a container having a plurality of wall which jointly define an inner chamber, a cover connected with said container turnably between an open position in which said inner chamber of said container is open and a closed position in which said inner chamber is closed, a plurality of compartments formed in said inner chamber of said container and including a compartment for accommodating a sprayer, a compartment for accommodating a mask, a compartment for accommodating at least one glove, a compartment for accommodating at least one encapsulant, and a compartment for accommodating a fungicide which compartments are separate from one another and are horizontally spaced from one another and do not communicate with one another, single compartment provided in said cover and extending substantially over a whole length of said cover and formed for storing a uniform, and means for locking said cover with said container and unlocking said cover from said container.

* * * * *